United States Patent
Xu et al.

(10) Patent No.: US 9,622,497 B2
(45) Date of Patent: Apr. 18, 2017

(54) CAROTENOID OIL SUSPENSION WITH HIGH BIOAVAILABILITY AND PREPARATION METHOD THEREOF

(75) Inventors: Xinde Xu, Donglu (CN); Bin Shao, Donglu (CN); Xuejun Lao, Donglu (CN)

(73) Assignee: Zhejiang Medicine Co., Ltd. Xinchang Pharmaceutical Factory (CN)

( * ) Notice: Subject to any disclaimer, the term of this patent is extended or adjusted under 35 U.S.C. 154(b) by 669 days.

(21) Appl. No.: 13/997,273

(22) PCT Filed: Jan. 30, 2011

(86) PCT No.: PCT/CN2011/000156
§ 371 (c)(1),
(2), (4) Date: Oct. 16, 2013

(87) PCT Pub. No.: WO2012/083571
PCT Pub. Date: Jun. 28, 2012

(65) Prior Publication Data
US 2014/0030419 A1 Jan. 30, 2014

(30) Foreign Application Priority Data
Dec. 23, 2010 (CN) .......... 2010 1 0602338

(51) Int. Cl.
| A23D 9/007 | (2006.01) |
| A61K 9/10 | (2006.01) |
| A61K 31/015 | (2006.01) |
| A61K 47/44 | (2017.01) |
| A23K 20/179 | (2016.01) |
| A23K 20/158 | (2016.01) |

(52) U.S. Cl.
CPC ............ *A23D 9/007* (2013.01); *A23K 20/158* (2016.05); *A23K 20/179* (2016.05); *A61K 9/10* (2013.01); *A61K 31/015* (2013.01); *A61K 47/44* (2013.01)

(58) Field of Classification Search
CPC ........... A23D 9/007; A23L 1/0029; B01J 2/02
USPC ......................................... 426/601; 514/684
See application file for complete search history.

(56) References Cited

U.S. PATENT DOCUMENTS

| 2003/0232892 A1* | 12/2003 | Guerra-Santos | ......... A61K 9/14 514/684 |
| 2004/0166199 A1* | 8/2004 | Kanner | ................ A23K 1/1606 426/52 |
| 2009/0041872 A1* | 2/2009 | Siegel | ................... A23L 1/0029 424/732 |

\* cited by examiner

*Primary Examiner* — Michele L Jacobson
*Assistant Examiner* — Bhaskar Mukhopadhyay
(74) *Attorney, Agent, or Firm* — McNeely, Hare & War, LLP

(57) ABSTRACT

A carotenoid oil suspension and preparation method thereof are provided. The method includes the following steps: a) mixing carotenoid with organic solvent, heating the mixture to dissolve the carotenoid sufficiently to obtain carotenoid solution; b) introducing the carotenoid solution obtained in step a) into a vegetable oil solution stirred in high speed by spraying, meanwhile recovering the organic solvent generated during spraying under vacuum condition, then, simultaneously completing recycling and spraying, thereafter, obtaining carotenoid oil suspension; wherein, the carotenoid oil suspension comprises a carotenoid crystal with an average particle size of less than 5 μm. The method is applicable in industrial scale with continuous operation and increased efficiency without additional carotenoid crystal grinding processes, and decreases the degradation of carotenoid during the preparation process of carotenoid oil suspension.

20 Claims, 1 Drawing Sheet

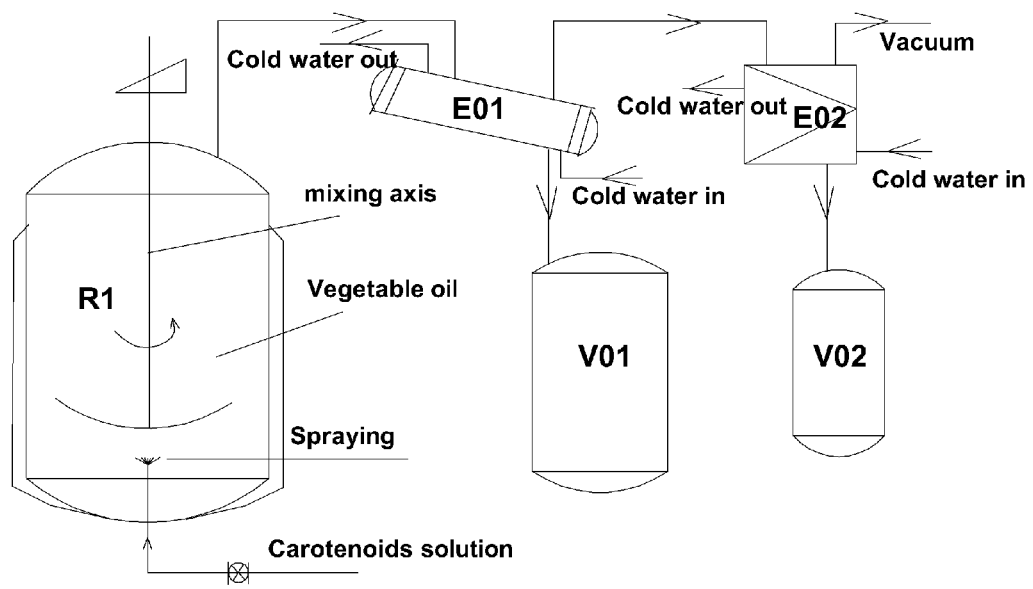

CAROTENOID OIL SUSPENSION WITH HIGH BIOAVAILABILITY AND PREPARATION METHOD THEREOF

CROSS-REFERENCE TO RELATED APPLICATIONS

This application claims priority to and is a National Phase Application under 35 USC 371 of PCT/CN2011/000156, filed on Jan. 30, 2011 (published as WO 2012/083571), which claims benefit of priority to CN 201010602338.6, filed on Dec. 23, 2010. The disclosures of the prior applications are considered part of and are incorporated by reference in their entirety in the disclosure of this application.

FIELD OF THE INVENTION

The present invention relates to a method of directly spraying a carotenoid solution to make a carotenoid crystal in the form of extremely fine particles suspended in a vegetable oil to obtain a carotenoid oil suspension with good fluidity and high bioavailability. It belongs to the field of biochemical engineering.

BACKGROUND OF THE INVENTION

Carotenoids exist widely in nature. Pigment in carbohydrates form was firstly crystallized and separated from the carrot roots by Wachenroder in 1831 and named as "carotene". After that, yellow polar pigments are separated and extracted from autumn leaves by Berzelius and named as "xanthophyll". With the development of biophysical technology, a series of natural pigments are separated by chromatographic method and named as "carotenoid". They have common chemical structural characteristics, and their molecular centers are all long chain of polyunsaturated polyisoprene. Many derivatives are produced by the means of cyclization, addition of oxygen or rotation of bond and isomerization. Currently, members of known carotenoids have about more than 600 species.

There are hundreds of carotenoids existed in the nature, but there have six species to be common and relatively large amounts, such as β-carotene, astaxanthin, canthaxanthin, lutein, zeaxanthin and lycopene. With the development of biotechnology and synthesis technology, many species of the six carotenoids have many different origins, for example, β-carotene may be obtained by synthesis, and also by fermentation method or cultivating Dunaliella, and also by extracting from natural substances, such as palm oil. Lycopene may be obtained by extracting from tomatoes or by fermentation, or also by synthesis. In these carotenoids, lutein is an exception, currently lutein is only obtained by extracting from plant but not by high cost synthesis method because of asymmetrical structure.

These six carotenoids which have similar molecular structures are a kind of hydrocarbons and oxygenated derivatives thereof. They are composed of eight isoprenoid units and only have small differences in a six-member ring at two ends. There are many chromophoric groups with conjugated double bond in the molecular structure of carotenoids, which gives carotenoid a special absorption area (blue light area) in ultraviolet-visible light area. Accordingly, crystal or solution of carotenoid possesses very glorious red, orange or yellow color under visible light. The color varies with different concentration. Carotenoids are deemed as a kind of pigments for a long time, those in autumn leaves and all sorts of colorful animals give people incomparable aesthetic feeling in nature. Meanwhile these conjugated double bonds also make carotenoid become a good free radical scavenger which has very strong activity of antioxidant and could effectively block free radical chain reaction in the cells. Thus, carotenoid has many kinds of special and important physiological functions.

β-carotene is the most wide and important carotenoids, and is a favourable provitamin A. According to the amount of Vitamin A in body, β-carotene could automatically decompose to supplement deficiency of Vitamin A. Lutein and zeaxanthin are isomers, and the only difference between them is the different site of a double bond on one of the six-member ring chain-terminating. They are only carotenoids existed in the human eye retina, and they are selectively deposited in the macular region and the whole retina, and their density is the highest around the central fovea of macula and gradually decreased around the retina. These macular pigments are able to effectively prevent from occurrence of oxidation reaction on the retina and have important protective effect on the retina. Lycopene has very good effect on prophylaxis and treatment of prostate disease. Astaxanthin also has important roles of anti-tumor and preventing cancer, etc. This is why lots of epidemiologic studies confirm that consuming fruits and vegetables containing carotenoid usually and regularly decrease risks of chronic diseases including cardiovascular disease, and meanwhile have beneficial effects on prophylaxis of cancer.

Therefore, nutritionists highly recommend that addition or preventive ingestion of antioxidant such as vitamin and carotenoid. Food and pharmaceutical market provide consumers a great quantity of the kind of "cell protective agent". Now various health foods added to single or many kinds of carotenoids are presented on the market, but the more effective means to supplement carotenoids for people is to ingest the materials in the form of dietary supplement, for example various tablets, hard capsules, soft capsules, etc. Usually only a grain of tablet or capsule can fulfill a day total requirement of carotenoid for one person. Concerning request of these ingestion way, many kinds of dosage forms of carotenoid are also presented on the market, for example microparticles CarolBeta® and CaroCare® rich in β-carotene, microencapsulation beadlets CarolGold® , FloraGlo® rich in xanthophyl, microparticle CarolZea® rich in zeaxanthin, microparticle Redivivo® rich in lycopene, etc. are suitable for tabletting or hard capsules; And there are some carotenoid oil suspensions suited to cover soft capsules. It is more convenient and popular methods by ingesting carotenoids in the form of soft capsules. Carotenoids usually exist in the form of oil suspensions when preparing soft capsules, that is, carotenoids are grinded to a certain degree of fineness and then suspended in a vegetable oil, so the fluidity of carotenoid oil suspensions determines the complexity of a production process. Methods of decreasing the viscosity of carotenoid oil suspensions have been disclosed by related patents.

On the other hand, it is very important for the particle size of the active ingredient in the carotenoid oil suspension, because which directly determines the level of bioavailability of the raw material oil suspension in soft capsule in body, the smaller carotenoid particle size means more easier absorption and utilization in body after ingestion, consequently, the smaller carotenoid particle size has the higher bioavailability. So people always try to reduce the carotenoid particle size in the oil suspension to reach to a level of micron even nanoscale, in order to make it have higher bioavailability after being filled into the soft capsule.

In addition, it is also important that excessive harmful organic solvents should be brought thereinto when ingesting carotenoids in the form of soft capsules. So it requires that organic solvents are used during as few steps as possible before carotenoids are filled into soft capsules and the organic solvents are inevitably used in certain steps removed in extra processes in order to make it meet requirements for human edible safety.

There are many methods of preparing for carotenoid oil suspensions in the previous documents. A common method is to sufficiently grind carotenoid crystals, and then mix the carotenoid powders grinded with a vegetable oil to obtain oil suspensions. However, the carotenoid crystals can't be grinded very fine by using the method, the particle size thereof is about 15 μm. It will eventually affect absorption and utilization of the oil suspension in body, and make the bioavailability more poorer. Besides it will inevitably cause temperature increasing of carotenoid crystals during grinding. Especially the increase of temperature will be more obvious when the particle size of carotenoids should be grinded to very fine, which will inevitably result in degradation and loss of carotenoids due to oxidization of carotenoids resulted from high temperature. So it would be undesirable to prepare for carotenoid oil suspensions by the method of grinding.

U.S. Pat. No. 6,936,279 B2 discloses a method of preparing for carotenoid oil suspensions. In particular, a carotenoid is firstly mixed with a water-insoluble solvent, and then to spray under nitrogen after mixing with a vegetable oil, to collect the sprayed solution and to recycle the solvent to obtain a carotenoid oil suspension. In the process, a large quantity of emulsifier and water are added in order to guarantee carotenoid particles no longer reaggregated after spraying, and then to stop spraying and to recover the solvent after collecting a certain amount of the sprayed "concentrate" in order to remove a large amount of organic solvents. It certainly results in industrial production disadvantageous, for the yield of the method is lower, and consequently the method is only suitable for laboratory preparation. Moreover, it is not very effective for preventing from reaggregation of carotenoid crystals in droplets, and the particle size of carotenoid crystals in oil suspension product is larger. More importantly, it is very difficult for sufficiently removing organic solvents due to existences of a large amount of emulsifier. It will certainly bring hidden trouble in safety of the final product in soft capsules. At the same time, there is no effective subsequent operation to remove the useless emulsifier for preparation of the oil suspension. It will cause waste and increase safety risks.

The present invention tried to find out a method of preparing for a carotenoid oil suspension with higher bioavailability. The carotenoid particles in the carotenoid oil suspensions obtained by the method of the present invention are very fine with the average diameter of less than 5 μm. So it is easily absorbed and utilized in the body, and there is no residual organic solvents in the product, and the product has very higher safety. Moreover, the process has higher industrial production efficiency and is suitable for continuous operations.

SUMMARY OF THE INVENTION

The purpose of the invention is to conveniently obtain a carotenoid oil suspension by using an efficient method without additional processes of super-finely grinding carotenoid crystals. In particular, carotenoids are directly dissolved in organic solvents and sprayed in a vegetable oil; and the same time the organic solvent in carotenoid oil suspensions is removed under vacuum during the process to make carotenoids precipitated in amorphous form. The carotenoid crystals precipitated will not reaggregate to make its size larger under high-speed stirring. It certainly ensures the carotenoid particles in carotenoid oil suspension are fine enough to be beneficially absorption and utilization in body, so as to have higher bioavailability.

According to one aspect of the invention, the present invention provides a method of preparing for a carotenoid oil suspension, the method comprises the following steps:

a) mixing a carotenoid with an organic solvent to obtain a mixture, heating the mixture to sufficiently dissolve the carotenoid to obtain a carotenoid solution; preferably, the heating temperature in step a) is 40° C.~60° C.; and b) introducing the carotenoid solution obtained in step a) into a vegetable oil solution in form of spraying under a high speed stirring, and in the meantime recovering the organic solvent generated during spraying under vacuum condition, then simultaneously completing spraying and recovering, thereafter, obtaining a carotenoid oil suspension.

Wherein the carotenoid oil suspension comprises a carotenoid crystal with an average particle size of less than 5 μm.

Preferably, the carotenoid is at least one selected from the group consisting of β-carotene, xanthophyll, zeaxanthin, lycopene, canthaxanthin and astaxanthin.

Preferably, the organic solvent is water-soluble organic solvent or water-insoluble organic solvent, the water-soluble organic solvent is acetone, tetrahydrofuran or isopropanol, the water-insoluble organic solvent is dichloromethane, toluene or ethyl acetate.

Preferably, the vegetable oil solution is one or more of edible vegetable oils selected from the group consisting of soybean oil, corn oil, sunflower oil, colza oil, peanut oil and safflower oil.

Preferably, the vegetable oil solution further comprises antioxidant, the antioxidant is one or more of edible antioxidants selected from the group consisting of mixed tocopherols, synthetic tocopherol, BHT, ethoxyquin and ascorbyl palmitate.

Preferably, the vegetable oil solution further comprises an organic solvent with less toxic or non-toxic, the organic solvent is ethanol, isopropanol or ethyl acetate.

Preferably, wherein heating the carotenoid solution and keeping at the temperature of 30° C.~70° C. before spraying into the vegetable oil solution under a high speed stirring, and during spraying process keeping a negative pressure state by vacuumizing.

According to another aspect of the invention, the present invention provides a carotenoid oil suspension, the carotenoid oil suspension comprises an edible carotenoid crystal with the average particle size of less than 5 μm prepared by the method and a vegetable oil solution. Wherein the carotenoid is at least one selected from the group consisting of β-carotene, xanthophyll, zeaxanthin, lycopene, canthaxanthin and astaxanthin. Preferably, the vegetable oil solution is one or more of edible vegetable oils selected from the group consisting of soybean oil, corn oil, sunflower oil, colza oil, peanut oil and safflower oil. Wherein the vegetable oil solution further comprises antioxidant. Preferably the antioxidant is one or more of edible antioxidants selected from the group consisting of mixed tocopherols, synthetic tocopherol, BHT, ethoxyquin and ascorbyl palmitate.

The process of the present invention is suitable for continuous operations in industrial production, and is with high production efficiency and without additional processes of grinding carotenoid crystals, as well as to reduce the degradation of carotenoids during the process of preparing for carotenoid oil suspensions. In the meantime the organic solvent is recovered under vacuum during spraying carotenoid crystal solutions, instead of removing the residual organic solvent in a separating step. Keeping the mixture of oil, carotenoid and organic solvent under high-speed stirring during spraying carotenoid oil suspensions, which can prevent from the reaggregation of amorphous carotenoid crystals, so as to guarantee the particle size of carotenoid small in oil suspension product with the average particle size of less than 5 μm.

BRIEF DESCRIPTION OF FIGURES

FIG. 1 shows the process diagram of preparing for the carotenoid oil suspension.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

As shown in FIG. 1, the process of the present invention is described as follows.

A carotenoid crystal is firstly mixed with a certain proportion of an organic solvent, and then heated to sufficiently dissolve the carotenoid crystal to form a carotenoid oil suspension, and afterwards the carotenoid oil suspension is introduced into a vegetable oil through spraying by a rapidly rotating nozzle from the bottom of reaction kettle R1. The vegetable oil comprises an antioxidant such as tocopherol, natural mixed tocopherols, BHT, ascorbyl palmitate, etc. More importantly, during the spraying process, the high-speed stirring can effectively prevent the amorphous carotenoid crystals from the reaggregation and would not make the particle size growing larger. In the process, the reaction kettle R1 is under vacuum. On the one hand, it can make the organic solvent volatilize and timely recover after spraying. On the other hand, it is beneficial for carotenoids crystals timely precipitated in amorphous form. Organic solvents are recovered into two tanks of V01 and V02 after passing through two condensers of E1 and E2, and can be repeated used.

The organic solvents in the process can be water-soluble such as acetone, tetrahydrofuran, ethanol, isopropanol, etc, or water-insoluble such as dichloromethane, toluene, ethyl acetate, etc. According to the solubility of carotenoid crystals in organic solvent, the ratio of organic solvent to crystals can be adjusted, to make carotenoid sufficiently dissolved in organic solvents.

The vegetable oil in the process can be one or more of edible vegetable oils selected from the group consisting of sunflower oil, soybean oil, colza oil, corn oil, peanut oil, or safflower oil according to different requirements of production. The weight ratio of a vegetable oil to a carotenoid crystal in reaction kettle can be adjusted according to the required concentration of carotenoid in carotenoid oil suspensiona. Moreover, according to the requirement, one part of vegetable oil can be placed in reaction kettle R1 and another part is mixed with organic solvent and carotenoid crystal to dissolve the carotenoid crystal. In some cases, especially when the content of carotenoid is required to be high in the carotenoid oil suspension, a certain amount of an organic solvent can be mixed into a vegetable oil in order to reduce the viscosity of solution in reaction kettle R1. The toxicity of the organic solvent is required to be low, and its boiling point is higher than that of the organic solvent for dissolving the carotenoid crystal. In the spraying process, the organic solvent for dissolving carotenoid crystals can be continuously removed under vacuum by controlling the jacket temperature of reaction kettle R1. But the organic solvent for reducing the viscosity of the solution could not or seldom be taken away. After completing spraying, raising the jacket temperature of reaction kettle R1, these organic solvents are recovered under vacuum. The suitable organic solvent may be ethanol, isopropanol, isobutyl acetate, etc. The effective concentration of carotenoid in the carotenoid oil suspension of the product can be adjusted from 5 wt. % to 50 wt. % according to the production requirement.

Carotenoid mentioned in the present invention comprises various of carotenoids suitable for human consumption in industrialized production, comprising natural and synthetic sources, such as β-carotene, xanthophyll, lycopene, canthaxanthin, zeaxanthin and astaxanthin or the mixture thereof.

EXAMPLE 1

18.3 kg xanthophyll crystal (content of 82.5%) is weighed and sufficiently mixed with 370 kg dichloromethane, the temperature is raised to 40° C. under stirring to dissolve the xanthophyll crystal to obtain a xanthophyll solution. Meanwhile, 273 kg soybean oil and 9 kg tocopherols is mixed in the reaction kettle R1, the temperature is raised to 30° C. and kept at the temperature, and vacuumized to keep a negative pressure state, and then stirred in a high-speed, the xanthophyll solution is sprayed by a rapidly rotating nozzle and introduced into soybean oil solution under a high-speed stirring, the organic solvent of dichloromethane in xanthophyll solution is sprayed and immediately volatilized under vacuum and then cooled into the tanks V01 and V02 after passing through the heat exchangers E01 and E02, and the organic solvent of dichloromethane may be circularly used.

The recovering of dichloromethane is finished when completion of spraying xanthophyll solution. 100 kg xanthophyll oil suspension is produced by the mixture in reactor kettle R1. Wherein the content of xanthophyll is 5.0 wt. %. The organic solvent in xanthophyll solution is volatilized under vacuum and the xanthophyll crystal can timely precipitated in amorphous form, However, the precipitated amorphous xanthophyll crystal is not to reaggregate to make the particle size grow larger, due to the high-speed stirring. So the average particle size of the xanthophyll crystal in the oil suspension is about 2 μm, and no residual solvent can be detected. Consequently it is very beneficial for absorption and utilization in body.

EXAMPLE 2

103 kg β-carotene crystal (content of 98.5%) is weighed and sufficiently mixed with 1000 kg tetrahydrofuran and 10 kg ascorbyl palmitate, the temperature is raised to 40° C. under stirring to dissolve the β-carotene crystal to obtain a β-carotene solution. Meanwhile, 90 kg sunflower oil and corn oil (w/w=1:1) is mixed into a reaction kettle R1, and 300 kg absolute alcohol is mixed into the reaction kettle in order to reduce the viscosity of solution, the temperature is raised to 40° C. and kept at the temperature, and vacuumized to keep a negative pressure state, and then stirred in a high-speed, the β-carotene solution is sprayed by a rapidly rotating nozzle and introduced into vegetable oil solution under a high-speed stirring, the organic solvent of tetrahydrofuran in β-carotene solution is sprayed and immediately volatilized under vacuum at this temperature, and then cooled into the tanks V01 and V02 after passing through the heat exchangers E01 and E02, and the organic solvent of tetrahydrofuran may be circularly used. The recovering of tetrahydrofuran is finished when completion of spraying β-carotene solution. Then the temperature of the mixture in reaction kettle is raised to 70° C., and the absolute alcohol therein is recovered under vacuum. 200 kg β-carotene oil suspension is produced by the mixture in reactor kettle R1. Wherein the content of β-carotene is 50.0 wt. %. The organic solvent in β-carotene solution is volatilized under vacuum and the β-carotene crystal can timely precipitate in amorphous form. However, the precipitated amorphous β-carotene crystal is not to reaggregate to make the particle size grow larger due to the high-speed stirring. So the average particle size of the β-carotene crystal in the oil suspension is about 3 μm. Consequently it is very beneficial for improvement of the bioavailability in body, and no residual solvent can be detected in the product.

EXAMPLE 3

74 kg zeaxanthin crystal (content of 81.5%) is weighed and sufficiently mixed with 1200 kg dichloromethane, the temperature is raised to 40° C. under stirring to dissolve the zeaxanthin crystal to obtain a zeaxanthin solution. Meanwhile, 211 kg colza oil and peanut oil (w/w=1:2) and 15 kg tocopherols is mixed to a reaction kettle R1, and 300 kg isopropanol is mixed into the reaction kettle in order to reduce the viscosity of solution, the temperature is raised to 30° C. and kept at the temperature, and vacuumized to keep a negative pressure state, and then stirred in a high-speed, the zeaxanthin solution is sprayed by a rapidly rotating nozzle and introduced into vegetable oil solution under a high-speed stirring, the organic solvent of dichloromethane in zeaxanthin solution is sprayed and immediately volatilized under vacuum at this temperature, and then cooled into the tanks V01 and V02 after passing through the heat exchangers E01 and E02, and the organic solvent of dichloromethane may be circularly used. The recovering of dichloromethane is finished when completion of spraying zeaxanthin solution. Then the temperature of the mixture in reaction kettle is raised to 80° C., and the isopropanol therein is recycled under vacuum. 300 kg zeaxanthin oil suspension is produced by the mixture in reactor kettle R1. Wherein, the content of zeaxanthin is 20.0 wt. %. The organic solvent in zeaxanthin solution is volatilized under vacuum and the zeaxanthin crystal can timely precipitate in amorphous form. However, the precipitated amorphous zeaxanthin crystal is not to reaggregate to make the particle size grow larger due to the high-speed stirring. So the average particle size of zeaxanthin crystal in the oil suspension is about 2.5 μm. It is very beneficial for improvement of the bioavailability in body.

EXAMPLE 4

26.0 kg lycopene crystal (content of 96.5%) is weighed and sufficiently mixed with 600 kg ethyl acetate, the temperature is raised to 60° C. under stirring to dissolve the lycopene crystal to obtain a lycopene solution. Meanwhile, 165 kg safflower oil and 9 kg antioxidant of BTH is mixed to a reaction kettle R1, the temperature is raised to 60° C. and kept at the temperature, and vacuumized to keep a negative pressure state, and then stirred in a high-speed, the lycopene solution is sprayed by a rapidly rotating nozzle and introduced into safflower oil solution under a high-speed stirring, the organic solvent of ethyl acetate in lycopene solution is sprayed and immediately volatilized under vacuum and then cooled into the tanks V01 and V02 after passing through the heat exchangers E01 and E02, and the organic solvent of ethyl acetate may be circularly used. The recovering of ethyl acetate is finished when completion of spraying lycopene solution. 200 kg lycopene oil suspension is produced by the mixture in reactor kettle R1. Wherein the content of lycopene is 12.5 wt. %. The organic solvent in lycopene solution is volatilized under vacuum and the lycopene crystal can timely precipitate in amorphous form. However, the precipitated amorphous lycopene crystal is not to reaggregate to make the particle size grow larger due to the high-speed stirring. So the average particle size of the lycopene crystal in the oil suspension is about 5 μm. Consequently it is very beneficial for absorption and utilization in body.

EXAMPLE 5

42.0 kg astaxanthin crystal (content of 95.2%) is weighed and sufficiently mixed with 1000 kg toluene and 9 kg antioxidant of ethoxy quinoline, the temperature is raised to 60° C. under stirring to dissolve the astaxanthin crystal to obtain a astaxanthin solution. Meanwhile, 159 kg sunflower oil is introduced to a reaction kettle R1, the temperature is raised to 70° C. and kept at the temperature, and vacuumized to keep a negative pressure state, and then stirred in a high-speed, the astaxanthin solution is sprayed by a rapidly rotating nozzle and introduced into vegetable oil solution under a high-speed stirring, the organic solvent of toluene in astaxanthin solution is sprayed and immediately volatilized under vacuum and then cooled into the tanks V01 and V02 after passing through the heat exchangers E01 and E02, and the organic solvent of toluene may be circularly used. The recovering of toluene is finished when completion of spraying astaxanthin solution. 200 kg astaxanthin oil suspension is produced by the mixture in reactor kettle R1. Wherein the content of astaxanthin is 20.0 wt. %. The organic solvent in astaxanthin solution is volatilized under vacuum and the astaxanthin crystal can timely precipitate in amorphous form. However, the precipitated amorphous astaxanthin crystal is not to reaggregate to make the particle size grow larger due to the high-speed stirring. So the average particle size of astaxanthin crystal in the oil suspension is about 4 μm. The oil suspension can be used in animal feed and is with higher bioavailability.

EXAMPLE 6

41 kg canthaxanthin crystal (content of 97.2%) is weighed and sufficiently mixed with 1800 kg acetone, the temperature is raised to 56° C. under stirring to dissolve the canthaxanthin crystal to obtain a canthaxanthin solution. Meanwhile, 56 kg corn oil and safflower oil (w/w=3:2) and 3 kg synthetic tocopherol is mixed to a reaction kettle R1, and 230 kg ethyl acetate is mixed into the reaction kettle in order to reduce the viscosity of solution, the temperature is raised to 50° C. and kept at the temperature, and vacuumized to keep a negative pressure state, and then stirred in a high-speed, the canthaxanthin solution is sprayed by a rapidly rotating nozzle and introduced into vegetable oil solution under a high-speed stirring, the organic solvent of acetone in canthaxanthin solution is sprayed and immediately volatilized under vacuum at this temperature and then cooled into the tanks V01 and V02 after passing through the heat exchangers E01 and E02, and the organic solvent of acetone may be circularly used. The recovering of acetone is finished when completion of spraying canthaxanthin solution. Then the temperature of the mixture in reaction kettle is raised to 80° C., and the ethyl acetate therein is recycled under vacuum. 100 kg of canthaxanthin oil suspension is produced by the mixture in reactor kettle R1. Wherein the content of canthaxanthin is 40.0 wt. %. The average particle size of canthaxanthin crystal in the oil suspension is about 4.2 μm. Consequently it is very beneficial for the improvement of bioavailability in body.

EXAMPLE 7

10 kg zeaxanthin crystal and 45 kg xanthophyll crystal is weighed and sufficiently mixed with 1800 kg dichloromethane, the temperature is raised to 40° C. under stirring to dissolve the crystal to obtain the solution of zeaxanthin and xanthophyll. Meanwhile, 142 kg colza oil and 3 kg tocopherols is mixed to a reaction kettle R1, and 300 kg ethanol is mixed into the reaction kettle in order to reduce the viscosity of solution, the temperature is raised to 30° C. and kept at the temperature, and vacuumized to keep a negative pressure state, and then stirred in a high-speed, the solution of xanthophyll and zeaxanthin is sprayed by a rapidly rotating nozzle and introduced into vegetable oil solution under a high-speed stirring, the organic solvent of dichloromethane in carotenoid solution is sprayed and immediately volatilized under vacuum at this temperature and then cooled into the tanks V01 and V02 after passing through the heat exchangers E01 and E02, and the organic solvent of dichloromethane may be circularly used. The recovering of dichloromethane is finished when completion of spraying carotenoid solution. Then the temperature of the mixture in reaction kettle is raised to 80° C., and the ethanol therein is recycled under vacuum. 200 kg oil suspensions of xanthophyll and zeaxanthin is produced by the mixture in reactor kettle R1. Wherein the content of zeaxanthin is 8.5 wt. % and the content of xanthophyll is 19.1%. The average particle size of xanthophyll crystal and zeaxanthin crystal in oil suspension is about 3.2 μm. Consequently it is very beneficial for the improvement of the bioavailability in body.

EXAMPLE 8

32 kg natural lycopene crystal and 92 kg natural β-carotene crystal is weighed and sufficiently mixed with 2600 kg tetrahydrofuran, the temperature is raised to 40° C. under stirring to dissolve the crystal to obtain the solution of lycopene and natural β-carotene. Meanwhile, 166 kg colza oil, soybean oil and safflower oil (w/w/w=1:1:1), 5 kg synthetic tocopherol and 5 kg tocopherols is mixed to a reaction kettle R1, and 400 kg ethyl acetate is mixed into the reaction kettle in order to reduce the viscosity of solution, the temperature is raised to 40° C. and kept at the temperature, and vacuumized to keep a negative pressure state, and then stirred in a high-speed, the solution of lycopene and natural β-carotene is sprayed by a rapidly rotating nozzle and introduced into vegetable oil solution under a high-speed stirring, the organic solvent of tetrahydrofuran in carotenoid solution is sprayed and immediately volatilized under vacuum at this temperature and then cooled into the tanks V01 and V02 after passing through the heat exchangers E01 and E02, and the organic solvent of tetrahydrofuran may be circularly used. The recovering of tetrahydrofuran is finished when completion of spraying carotenoid solution. The temperature of the mixture in reaction kettle is raised to 80° C., and the ethyl acetate therein is recycled under vacuum. 300 kg oil suspension of lycopene and natural β-carotene is produced by the mixture in reactor kettle R1. Wherein the content of lycopene is 10.5 wt. % and the content of natural β-carotene is 30.1 wt. %. The average particle size of lycopene crystal and natural β-carotene crystal in the oil suspension is about 2.7 μm, and no harmful residual organic solvent can be detected. Consequently it is very beneficial for the improvement of the bioavailability in body.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A method of preparing a carotenoid oil suspension comprising the steps of:
    a) mixing a carotenoid with an organic solvent to obtain a mixture, heating the mixture at a temperature to sufficiently dissolve the carotenoid to obtain a carotenoid solution; and
    b) introducing the carotenoid solution obtained in step a) into a vegetable oil solution under a high speed stirring by spraying, and in the meantime recovering the organic solvent generated during spraying under vacuum condition, then simultaneously completing recovering and spraying, thereafter, obtaining a carotenoid oil suspension; wherein the carotenoid oil suspension comprises a carotenoid crystal with an average particle size of less than 5 μm, and the organic solvent is a water-soluble organic solvent or water-insoluble organic solvent.

2. The method according to claim 1, wherein heating the mixture of step a) at a temperature to sufficiently dissolve the carotenoid to obtain a carotenoid solution comprises heating the mixture at a temperature of 40° C. to 60° C.

3. The method according to claim 1, wherein the carotenoid is at least one selected from the group consisting of β-carotene, xanthophyll, zeaxanthin, lycopene, canthaxanthin and astaxanthin; the vegetable oil solution is one or more of edible vegetable oils selected from the group consisting of soybean oil, corn oil, sunflower oil, colza oil, peanut oil and safflower oil.

4. The method according to claim 3, wherein the carotenoid crystal has an average particle size of 2.5 μm, 2.7 μm, 3 μm or 3.2 μm.

5. The method according to claim 4, wherein the carotenoid is at least one selected from the group consisting of β-carotene, xanthophyll, zeaxanthin, lycopene, canthaxanthin and astaxanthin; and
    the vegetable oil solution is one or more of edible vegetable oils selected from the group consisting of soybean oil, corn oil, sunflower oil, colza oil, peanut oil and safflower oil.

6. The method according to claim 3, wherein the vegetable oil solution further comprises antioxidant, the antioxidant is one or more of edible antioxidants selected from the group consisting of mixed tocopherols, synthetic tocopherol, BHT, ethoxyquin and ascorbyl palmitate.

7. The method according to claim 6, wherein the carotenoid crystal has an average particle size of 2.5 μm, 2.7 μm, 3 μm or 3.2 μm.

8. The method according to claim 7, wherein the carotenoid is at least one selected from the group consisting of β-carotene, xanthophyll, zeaxanthin, lycopene, canthaxanthin and astaxanthin; and
the vegetable oil solution is one or more of edible vegetable oils selected from the group consisting of soybean oil, corn oil, sunflower oil, colza oil, peanut oil and safflower oil.

9. The method according to claim 6, wherein the vegetable oil solution further comprises ethanol, isopropanol or ethyl acetate with less toxicity or non-toxic.

10. The method according to claim 9, wherein the carotenoid crystal has an average particle size of 2.5 μm, 2.7 μm, 3 μm or 3.2 μm.

11. The method according to claim 10, wherein the carotenoid is at least one selected from the group consisting of β-carotene, xanthophyll, zeaxanthin, lycopene, canthaxanthin and astaxanthin; and
the vegetable oil solution is one or more of edible vegetable oils selected from the group consisting of soybean oil, corn oil, sunflower oil, colza oil, peanut oil and safflower oil.

12. The method according to claim 1, wherein the water-soluble organic solvent is acetone, tetrahydrofuran or isopropanol, the water-insoluble organic solvent is dichloromethane, toluene or ethyl acetate.

13. The method according to claim 12, wherein the carotenoid crystal has an average particle size of 2.5 μm, 2.7 μm, 3 μm or 3.2 μm.

14. The method according to claim 13, wherein the carotenoid is at least one selected from the group consisting of β-carotene, xanthophyll, zeaxanthin, lycopene, canthaxanthin and astaxanthin; and
the vegetable oil solution is one or more of edible vegetable oils selected from the group consisting of soybean oil, corn oil, sunflower oil, colza oil, peanut oil and safflower oil.

15. The method according to claim 1, further comprising heating the vegetable oil solution and keeping at the temperature of 30° C. ~70° C. before introducing the carotenoids solution into the vegetable oil solution.

16. The method according to claim 15, wherein the carotenoid crystal has an average particle size of 2.5 μm, 2.7 μm, 3 μm or 3.2 μm.

17. The method according to claim 16, wherein the carotenoid is at least one selected from the group consisting of β-carotene, xanthophyll, zeaxanthin, lycopene, canthaxanthin and astaxanthin; and
the vegetable oil solution is one or more of edible vegetable oils selected from the group consisting of soybean oil, corn oil, sunflower oil, colza oil, peanut oil and safflower oil.

18. The method according to claim 1, wherein the carotenoid crystal has an average particle size of 2.5 μm, 2.7 μm, 3 μm or 3.2 μm.

19. The method according to claim 18, wherein the carotenoid is at least one selected from the group consisting of β-carotene, xanthophyll, zeaxanthin, lycopene, canthaxanthin and astaxanthin; and
the vegetable oil solution is one or more of edible vegetable oils selected from the group consisting of soybean oil, corn oil, sunflower oil, colza oil, peanut oil and safflower oil.

20. The method according to claim 19, wherein the vegetable oil solution further comprises an edible antioxidant, selected from the group consisting of mixed tocopherols, synthetic tocopherol, BHT, ethoxyquin and ascorbyl palmitate.

* * * * *